United States Patent
Martin

(10) Patent No.: US 7,378,550 B2
(45) Date of Patent: May 27, 2008

(54) PROCESS FOR PREPARING REVERSE TRANSCRIPTASE INHIBITORS

(75) Inventor: Michael Tolar Martin, Durham, NC (US)

(73) Assignee: SmithKline Beecham Corporation, Philadelphia, PA (US)

(\*) Notice: Subject to any disclaimer, the term of this patent is extended or adjusted under 35 U.S.C. 154(b) by 295 days.

(21) Appl. No.: 10/550,255

(22) PCT Filed: Mar. 26, 2004

(86) PCT No.: PCT/US2004/009375

§ 371 (c)(1),
(2), (4) Date: Sep. 22, 2005

(87) PCT Pub. No.: WO2004/087881

PCT Pub. Date: Oct. 14, 2004

(65) Prior Publication Data

US 2006/0183944 A1    Aug. 17, 2006

Related U.S. Application Data

(60) Provisional application No. 60/458,144, filed on Mar. 27, 2003.

(51) Int. Cl.
    *C07D 303/00*    (2006.01)

(52) U.S. Cl. .......................................... 564/86; 564/87
(58) Field of Classification Search .................. 564/86, 564/87
    See application file for complete search history.

(56) References Cited

U.S. PATENT DOCUMENTS 3,828,078 A    8/1974    Mrozik

FOREIGN PATENT DOCUMENTS

WO    WO 01/17982        3/2001
WO    02/070470 A2    9/2002

OTHER PUBLICATIONS

Balzarini, "Suppression of resistance to drugs targeted to human immunodeficiency virus reverse transcriptase by combination therapy," *Biochemical Pharmacology* 58(1):1-27 (Jun. 1999).
De Clercq, "Perspectives of non-nucleoside reverse transcriptase inhibitors (NNRTIs) in the therapy of HIV-1 infection," *Il Famaco* 54:26-45 (1999).
Wyatt, Paul G., "Benzophenone Derivatives: A Novel Series of Potent and Selective Inhibitors of Human Immunodeficiency Virus Type 1 Reverse Transcriptase.", J. Med. Chem., 1995, 38, pp. 1657-1665.

*Primary Examiner*—J. Parsa
(74) *Attorney, Agent, or Firm*—Karen L. Prus

(57) ABSTRACT

The present invention is directed to processes for the synthesis of intermediates useful in the preparation of non-nucleoside reverse transcriptase inhibitors.

11 Claims, No Drawings

PROCESS FOR PREPARING REVERSE TRANSCRIPTASE INHIBITORS

CROSS-REFERENCE TO RELATED APPLICATIONS

This application is filed pursuant to 35 U.S.C. § 371 as a U.S. National Phase Application of International Application No. PCT/US2004/009375 filed Mar. 26, 2004, which claims priority from U.S. Provisional Application No. 60/458,144 filed Mar. 27, 2003.

BACKGROUND OF THE INVENTION

The human immunodeficiency virus ("HIV") is the causative agent for acquired immunodeficiency syndrome ("AIDS"), a disease characterized by the destruction of the immune system, particularly of CD4+ T-cells, with attendant susceptibility to opportunistic infections, and its precursor AIDS-related complex ("ARC"), a syndrome characterized by symptoms such as persistent generalized lymphadenopathy, fever and weight loss. HIV is a retrovirus; the conversion of its RNA to DNA is accomplished through the action of the enzyme reverse transcriptase. Compounds that inhibit the function of reverse transcriptase inhibit replication of HIV in infected cells. Such compounds are useful in the prevention or treatment of HIV infection in humans.

Non-nucleoside reverse transcriptase inhibitors (NNRTIs), in addition to the nucleoside reverse transcriptase inhibitors gained a definitive place in the treatment of HIV-1 infections. The NNRTIs interact with a specific site of HIV-1 reverse transcriptase that is closely associated with, but distinct from, the nucleoside binding site on reverse transcriptase. NNRTIs, however, are notorious for rapidly eliciting resistance due to mutations of the amino acids surrounding the NNRTI-binding site (E. De Clercq, *Il Famaco* 54, 26-45, 1999). Failure of long-term efficacy of NNRTIs is often associated with the emergence of drug-resistant virus strains (J. Balzarini, *Biochemical Pharmacology*, Vol 58, 1-27, 1999). Moreover, the mutations that appear in the reverse transcriptase enzyme frequently result in a decreased sensitivity to other reverse transcriptase inhibitors, which results in cross-resistance.

WO 00117982 discloses a series of benzophenone derivatives that when administered in vivo provide compounds that are useful as inhibitors of both wild type and mutant variants of HIV reverse transcriptase. Current methods for the preparation of certain intermediates useful in the synthesis of benzophenone compounds involve multi-step processes that are difficult to perform on large-scale and therefore are unsuitable for manufacture. The present invention features a process for the preparation of intermediates that can be carried out in a single step, that involve no toxic reagents, and are suitable for large-scale manufacture.

SUMMARY OF THE INVENTION

The present invention features a process for preparing a compound of formula (I)

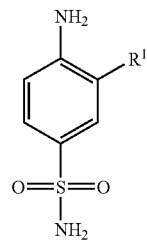

(I)

wherein
R$^1$ is selected from the group consisting of hydroxy, halogen, —CF$_3$, —NO$_2$ and C$_{1-8}$ alkyl, and C$_{1-8}$alkoxy comprising
i) reacting a compound of formula (IV)

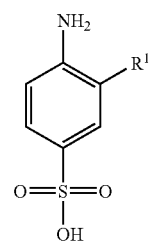

(IV)

with a suitable formamide in the presence of solvent and a chlorinating agent to form a compound of formula (III)

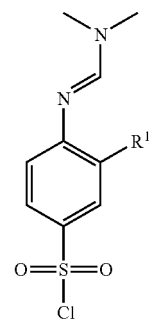

(III)

ii) reacting a compound of formula (III) with a solvent and ammonia to form a compound of formula (II),

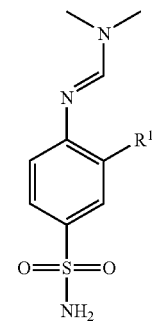

(II)

iii) deprotecting the compound of formula (II) to form a compound of formula (I).

DETAILED DESCRIPTION OF THE INVENTION

The present invention features a process for preparing a compound of formula (I)

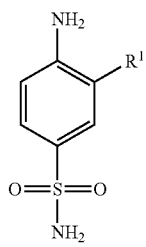

(I)

wherein
R$^1$ is selected from the group consisting of hydroxy, halogen, —CF$_3$, —NO$_2$ and C$_{1-8}$alkyl, and C$_{1-8}$alkoxy comprising
i) reacting a compound of formula (IV)

(IV)

with a suitable formamide in the presence of solvent and a chlorinating agent to form a compound of formula (III)

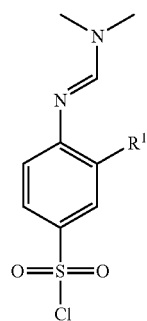

(III)

ii) reacting a compound of formula (III) with a solvent and ammonia to form a compound of formula (II),

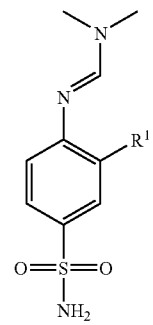

(II)

iii) deprotecting the compound of formula (II) to form a compound of formula (I).

As used herein, the term "alkyl", alone or in combination with any other term, refers to a straight-chain or branched-chain saturated aliphatic hydrocarbon radical containing the specified number of carbon atoms. Examples of alkyl radicals include, but are not limited to, methyl, ethyl, n-propyl, isopropyl, n-butyl, isobutyl, sec-butyl, tert-butyl, pentyl, isoamyl, n-hexyl and the like.

The term "alkoxy" refers to an alkyl ether radical, wherein the term "alkyl" is defined above. Examples of suitable alkyl ether radicals include, but are not limited to, methoxy, ethoxy, n-propoxy, isopropoxy, n-butoxy, isobutoxy, sec-butoxy, tert-butoxy and the like, with methoxy being preferred.

The term "halogen" refers to fluorine, chlorine, bromine or iodine.

The present invention features a process comprising i) reacting a compound of formula (IV) with N,N-dimethylformamide in the presence of methylene chloride and oxalyl chloride to form a compound of formula (III); ii reacting a compound of formula (III) with dimethoxyethane and ammonium hydroxide to form a compound of formula (II); and deprotecting a compound of formula (II) to form a compound of formula (I).

The present invention further features a process for the preparation of a compound of formula (V)

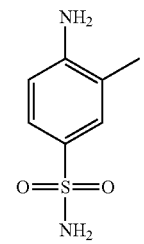

(V)

comprising:
i) reacting a compound of formula (VIII)

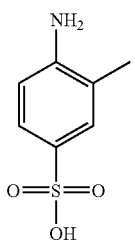

(VIII)

with N,N-dimethylformamide in the presence of solvent and a chlorinating agent to form a compound of formula (VII)

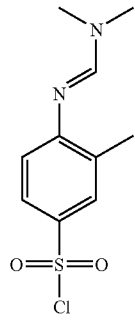

(VII)

ii) reacting a compound of formula (VII) with a solvent and ammonium hydroxide to form a compound of formula (VI),

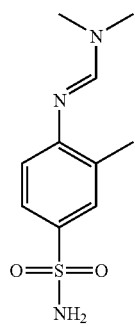

ii) deprotecting the compound of formula (VI) for form a compound of formula (V).

The present invention also features a process for the preparation of a compound of formula (V) wherein the solvent of step i) is dichloromethane, the chlorinating agent is oxalyl chloride, the ammonia is ammonia hydroxide, and the solvent of step ii) is dimethoxyethane.

Step i) of processes of the present invention may be carried out by treating the compound of formula (IV) with an amide such as N,N-dimethylformamide, in a suitable solvent selected from, chloroform, toluene, dimethoxyethane, tetrahydrofuran or dioxane or preferably methylene chloride and a halogenating agent, for example, a chlorinating agent, such as thionyl chloride, phosphoryl chloride, phosphorous pentachloride or bromide equivalents or preferably oxalyl chloride. The reaction may be carried out at a temperature in the range of 0° to reflux, about 20° C. to reflux temperature, most preferably in the range 25° C., with methylene chloride as the solvent.

Step ii) of the processes of the present invention may be carried out in a suitable solvent selected from an solvent such as tetrahydrofuran, dioxane or preferably dimethoxyethane. The reaction may be carried out by treating a mixture of the resultant compound of step i) with a source of ammonia such as ammonia gas, methanolic ammonia, preferably ammonium hydroxide, or any other suitable solution of ammonia. The reaction may be carried out at atmospheric pressure.

The step ii) product may be hydrolysed to the compound of formula (I) by treatment with a solution of base such as sodium, potassium, or calcium hydroxide, or preferably lithium hydroxide, in a water based solvent system with a suitable co-solvent such as methanol of other alcohol or water miscible ether. The compound of formula (I) can be isolated from the reaction solvent by adjustment of the reaction solution pH with a suitable acid source such as sulphuric or preferable hydrochloric acid.

Suitable chlorinating agents may be oxalyl chloride, thionyl chloride, or phosphoryl chloride.

Advantageously, an aqueous ammonia, such as ammonium hydroxide, or non aqueous ammonia source such as $NH_3$ gas or methanolic ammonia may be used.

Suitable solvents include dimethoxyethane, tetrahydrofuran, and dioxane.

Advantages of the processes of the present invention may include the simultaneous in situ protection and activation followed by immediate conversion to sulphonamide. In the processes of the present invention, the activating agent may also be the protecting agent.

The following scheme, Scheme A, represents the process according to a feature of the present invention and is not intended to limit the scope of the invention but is provided for illustration only.

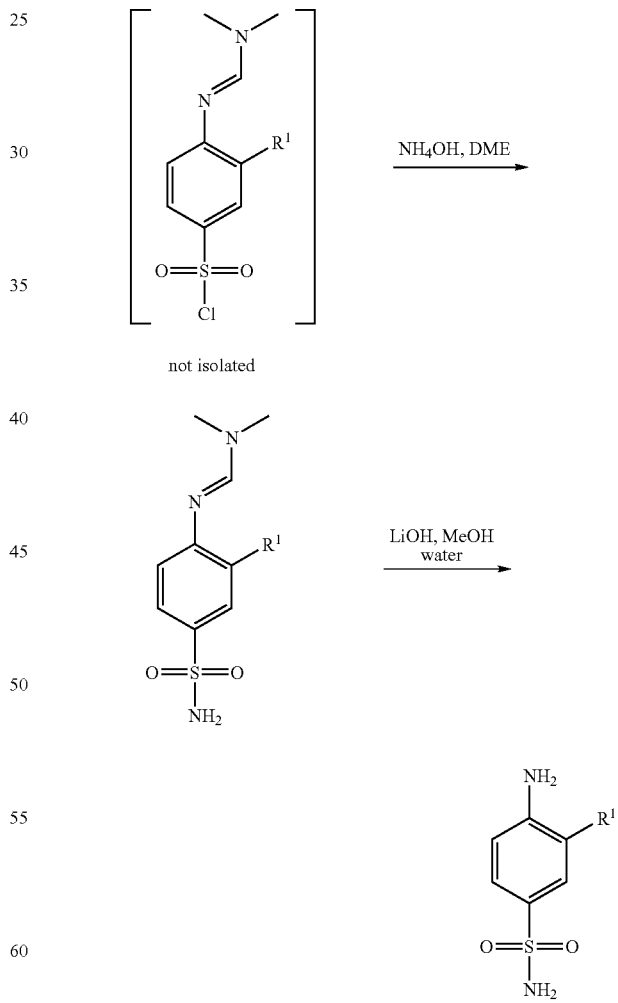

Scheme A wherein
R$^1$ is selected from the group consisting of hydroxy, halogen, —CF$_3$, —NO$_2$ and C$_{1-8}$alkyl, C$_{1-8}$alkoxy.

The present invention also features the processes as hereindescribed wherein $R^1$ is $C_{1-8}$alkyl. An embodiment is illustrated in Scheme B.

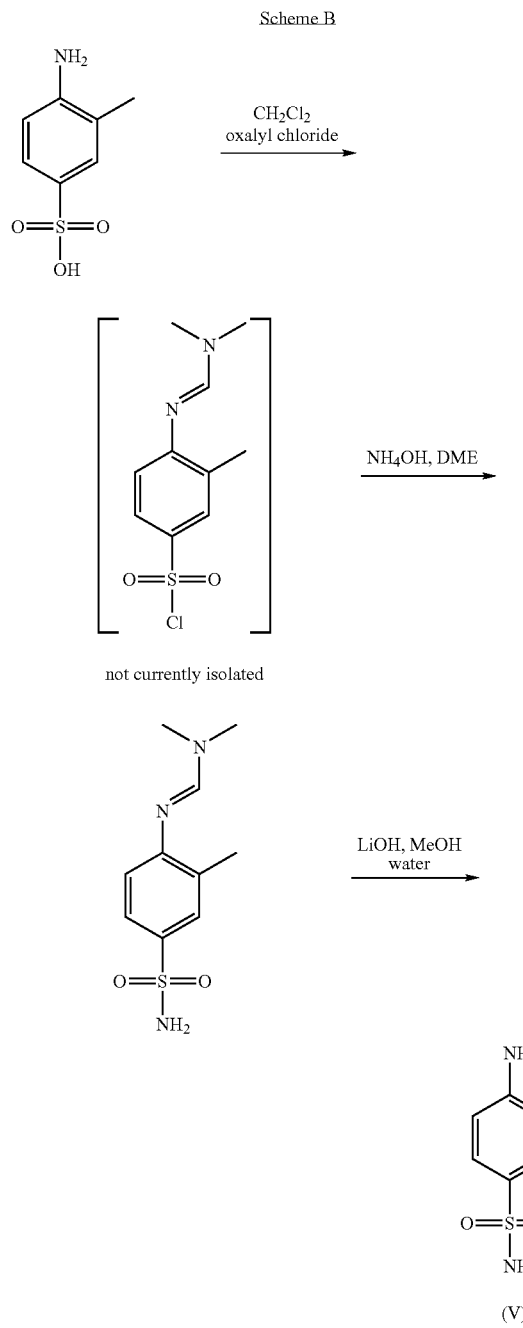

not currently isolated

EXAMPLE 1

To a mixture of 2-aminotoluene-5-sulfonic acid (1.0 wt, 1.0 eq. 6.41 mol) in dichloromethane (15 vol) and N,N-dimethylformamid (0.43 wt, 1.1 equiv.,) was added oxalyl chloride (1.53 wt, 2.25 equiv.) over a period of 120 minutes. Additional dichloromethane (1 volume) was added and the resulting mixture stirred at ambient temp 3 hours. IPC of methanol-quenched aliquot (TLC, 8% MeOH-DCM and HPLC normal phase fast LC) showed complete conversion to activated, protected intermediate. Methylene chloride was removed under gentle reflux at atmospheric pressure to approximately 5 volumes and replaced with dimethoxyethane (7.5 vol). The mixture was evaporated under vacuum with a jacket temperature of 65 degrees to approximately 5 volumes and diluted with additional DME (2.5 volumes). The resulting mixture was cooled to 15 degrees and treated with a solution of 28% ammonium hydroxide (2.23 vol., 3 equiv.) added over a period of 15 minutes which results in momentary dissolution of the intermediate followed quickly by precipitation of the protected intermediate. IPC (TLC, normal phase fast LC) showed complete conversion to protected sulphonamide. The intermediate was filtered, and the solid washed with water (2×1 vol), and then placed back in the reactor. The reactor was charged with a solution of LiOH (0.45 wt., 2 equiv) in 9:1 water:methanol (8 vol based on original input). The resulting solution was warmed to 50 degrees for 5 hours or until IPC (TLC and normal phase fast LC) showed complete hydrolysis to a compound of formula (V). Decolorizing carbon (1.0 weight %) and celite (5.0 weight %) was added and the mixture stirred briefly and filtered through filter cloth into reactor B. The solution was cooled to 25 degrees and adjusted to pH 9 with addition 6 N hydrochloric acid (approximately 1.6 vol.) over a period of 15 minutes with vigorous stirring. The solution was maintained at 45 to 55 degrees for a 2 to 4 hour period to allow conversion from the original amorphous precipitate to a crystalline solid, then cooled to 20 degrees and filtered. The resulting crystalline solid was washed with 90% water/methanol (1 volume) followed by water (2×1 volumes) and dried in vacuum oven at 50 degrees with nitrogen sweep for 16 hours.

What is claimed is:
1. A process for the preparation of a compound of formula (I)

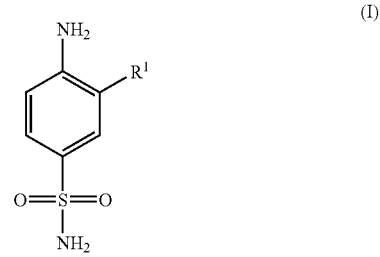

wherein
$R^1$ is selected from the group consisting of hydroxy, halogen, $-CF_3$, $-NO_2$, $C_{1-8}$alkyl, and $C_{1-8}$alkoxy comprising
i) reacting a compound of formula (IV)

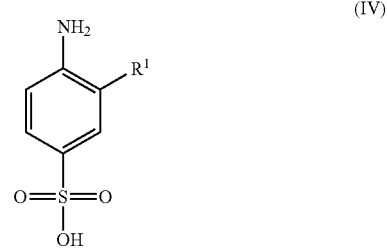

with a suitable formamide in the presence of solvent and a chlorinating agent to form a compound of formula (III)

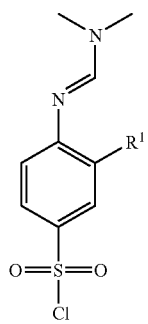

(III)

ii) reacting a compound of formula (III) with a solvent and ammonia to form a compound of formula (II),

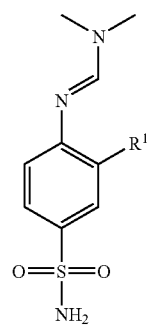

(II)

iii) deprotecting the compound of formula (II) to form a compound of formula (I).

2. A process according to claim 1 wherein $R^1$ is $C_{1-8}$alkyl.

3. A process for the preparation of a compound of formula (I)

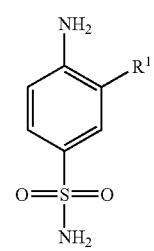

(I)

wherein
R¹ is selected from the group consisting of hydroxy, halogen, —CF₃, —NO₂, C₁₋₈alkyl, and C₁₋₈alkoxy comprising i) reacting a compound of formula (IV)

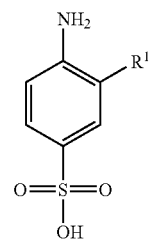

(IV)

with N,N-dimethylformamide in the presence of methylene chloride and oxalyl chloride to form a compound of formula (III)

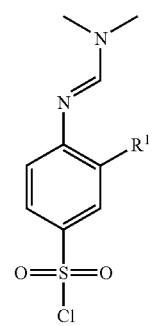

(III)

ii) reacting a compound of formula (III) with dimethoxyethane and ammonia to form a compound of formula (II),

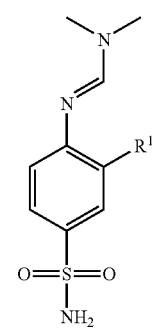

(II)

iii) deprotecting the compound of formula (II) to form a compound of formula (I).

4. A process according to claim 3 wherein $R^1$ is $C_{1-8}$alkyl.

5. A process according to claim 1 wherein the solvent of step i) is selected from the group consisting of chloroform, toluene, dimethoxyethane, tetrahydrofuran, dioxane, and methylene chloride.

6. A process according to claim 1 wherein the chlorinating agent is selected from the group consisting of thionyl chloride, phosphoryl chloride, and oxalyl chloride.

7. A process according to claim 1 wherein the solvent of step ii) is selected from the group consisting of tetrahydrofuran, dioxane, and dimethoxyethane.

8. A process according to claim 1 wherein the ammonia is selected from ammonia gas, methanolic ammonia, and ammonium hydroxide.

9. A process according to claim 3 wherein the ammonia is selected from ammonia gas, methanolic ammonia, and ammonium hydroxide.

10. A process for the preparation of the compound of formula (V)

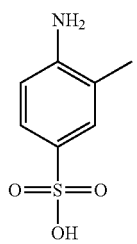

(V)

comprising:

i) reacting a compound of formula (VIII)

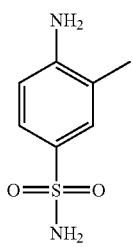

(VIII)

with N,N-dimethylformamide in the presence of solvent and a chlorinating agent to form a compound of formula (VII)

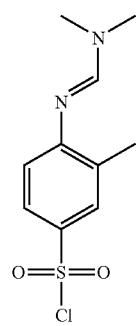

(VII)

ii) reacting a compound of formula (VII) with a solvent and ammonium hydroxide to form a compound of formula (VI),

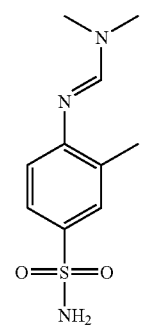

(VI)

iii) deprotecting the compound of formula (VI) for form a compound of formula (V).

11. The process according to claim 10, wherein the solvent of step i) is dichloromethane, the chlorinating agent is oxalyl chloride, the ammonia is ammonia hydroxide, and the solvent of step ii) is dimethoxyethane.

* * * * *